US010094839B2

(12) United States Patent
McBride et al.

(10) Patent No.: US 10,094,839 B2
(45) Date of Patent: Oct. 9, 2018

(54) BIOMARKER OF RENAL DYSFUNCTION

(71) Applicants: The Queen's University of Belfast, Belfast (GB); BELFAST HEALTH AND SOCIAL CARE TRUST, Belfast (GB)

(72) Inventors: William Thomas McBride, Belfast (GB); Marilyn Armstrong, Ballyhalbert (GB)

(73) Assignees: THE QUEEN'S UNIVERSITY OF BELFAST, Belfast (GB); BELFAST HEALTH AND SOCIAL CARE TRUST, Belfast (GB)

( * ) Notice: Subject to any disclaimer, the term of this patent is extended or adjusted under 35 U.S.C. 154(b) by 0 days.

(21) Appl. No.: 14/407,760

(22) PCT Filed: Jun. 13, 2013

(86) PCT No.: PCT/GB2013/051553
§ 371 (c)(1),
(2) Date: Dec. 12, 2014

(87) PCT Pub. No.: WO2013/186564
PCT Pub. Date: Dec. 19, 2013

(65) Prior Publication Data
US 2015/0126480 A1 May 7, 2015

(30) Foreign Application Priority Data

Jun. 14, 2012 (GB) .................................. 1210587.0

(51) Int. Cl.
*A61K 38/00* (2006.01)
*G01N 33/493* (2006.01)
*G01N 33/68* (2006.01)
*A61B 5/20* (2006.01)

(52) U.S. Cl.
CPC ......... *G01N 33/6863* (2013.01); *A61B 5/201* (2013.01); *G01N 33/6869* (2013.01); *G01N 2333/525* (2013.01); *G01N 2333/545* (2013.01); *G01N 2333/7151* (2013.01); *G01N 2333/7155* (2013.01); *G01N 2800/347* (2013.01); *G01N 2800/50* (2013.01)

(58) Field of Classification Search
None
See application file for complete search history.

(56) References Cited

U.S. PATENT DOCUMENTS

| 5,041,381 A * | 8/1991 | Abrams | C07K 14/5406 435/335 |
| 7,476,497 B2 * | 1/2009 | Hu | G01N 33/57442 435/4 |
| 2011/0071121 A1 | 3/2011 | McBride et al. | |
| 2015/0183025 A1 | 7/2015 | Aoki | |

FOREIGN PATENT DOCUMENTS

| EP | 1962092 A2 | 8/2008 |
| JP | 2012-506537 A | 3/2012 |
| WO | WO-2009/130505 A1 | 10/2009 |
| WO | WO-2010/068686 A2 | 6/2010 |

OTHER PUBLICATIONS

Pelikanova et al 2003. Diabetologia 46:470-4.*
Makela et al. 2004. Am J. Kidney Disease. 43:809-816.*
McBride, William T., et al.; "Acute Renal Failure"; Surgery, vol. 27, No. 11; Nov. 1, 2009; pp. 480-485.
McBride, William T., et al.; "Cytokine Phenotype, Genotype, and Renal Outcomes at Cardiac Surgery"; Cytokine, vol. 61; Nov. 5, 2012; pp. 275-584.
Miyazawa, Itsuko, et al.; "Association between Serum Soluble TNFα Receptors and Renal Dysfunction in Type 2 Diabetic Patients without Proteinuria"; Diabetes Research and Clinical Practice, vol. 92; Feb. 1, 2011; pp. 174-180.
Markewitz, Boaz A., et al.; "Cytokine-Induced Expression of a Nitric Oxide Synthase in Rat Renal Tubule Cells"; J. Clin. Invest, vol. 91; May 1993; pp. 2138-2143.
Chatterjee, Prabal K., et al.; "Cytokine-Stimulated Nitric Oxide Production in the Human Renal Proximal Tubule and its Modulation by Natriuretic Peptides: a Novel Immunomodulatory Mechanism?"; Experimental Nephrology, vol. 7; 1999; pp. 438-448.
Gormley, S.M.C., et al.; "Plasma and Urinary Cytokine Homeostasis and Renal Function during Cardiac Surgery without Cardiopulmonary Bypass"; Cytokine, vol. 17, No. 2; Jan. 2002; pp. 61-65.
Litalien, Catherine, et al.; "Circulating Inflammatory Cytokine Levels in Hemolytic Uremic Syndrome"; Pediatric Nephrology, vol. 13; 1999; pp. 840-845.
Henkel, Gretchen; "Do Proinflammatory Cytokines Play a Role in Renal Dysfunction after Bypass?"; Anesthesiology, vol. 93, No. 5; Nov. 2000; p. 5.
Gormley, Sheena M.C., et al.; "Plasma and Urinary Cytokine Homeostasis and Renal Dysfunction during Cardiac Surgery"; Anesthesiology, vol. 93, No. 5; Nov. 2000; pp. 1210-1216.
Mishra, Jaya, et al.; "Neutrophil Gelatinase-Associated Lipocalin (NGAL) as a Biomarker for Acute Renal Injury after Cardiac Surgery"; The Lancet, vol. 365; Apr. 2, 2005; pp. 1231-1238.
Kopple, Joel D., et al.; "Nutritional Status of Patients with Different Levels of Chronic Renal Insufficiency"; Kidney International, vol. 36, Suppl. 27; 1989; pp. S-184-S-194.
Bihorac, Azra, et al.; "Acute Kidney Injury is Associated with Early Cytokine Changes after Trauma"; J Trauma Acute Care Surg., vol. 74, No. 4; Apr. 2013; pp. 1005-1013.
Luis Alves, Dulce, "International Search Report," prepared for PCT/GB2013/051553, dated Aug. 22, 2013, six pages.
Opal, Steven M., et al.; "Anti-Inflammatory Cytokines"; Chest, vol. 117, No. 4; Apr. 2000; pp. 1162-1172.
Brinkman, R. et al., "Acute Kidney Injury in Patients Undergoing Open Abdominal Aortic Aneurysm Repair: A Pilot Observation Trail", Journal of Cardiothoracic and Vascular Anesthesia, vol. 29 No. 5, Oct. 2015, pp. 1212-1219, electronic publication date Apr. 1, 2015.
U.S. Appl. No. 14/407,603, filed Dec. 12, 2014, McBride et al.
Luis Alves, Dulce, "International Search Report" for PCT/GB2013/051554, dated Sep. 3, 2013, 6 pages.

* cited by examiner

*Primary Examiner* — Shulamith H Shafer
(74) *Attorney, Agent, or Firm* — Winstead PC

(57) ABSTRACT

The present invention relates to a method for a method for predicting the development of renal dysfunction in a subject following physical trauma, hypotension, sepsis and/or septic shock syndrome, wherein the method comprises the steps of: —a. determining the level of an anti-inflammatory cytokine present in a sample taken from the subject after physical trauma, after a hypotensive event, after sepsis, and/or after septic shock syndrome; b. predicting the development in the subject of renal dysfunction on the basis of the level of an anti-inflammatory cytokine determined in step a).

1 Claim, 3 Drawing Sheets

BIOMARKER OF RENAL DYSFUNCTION

The present invention relates to a method for predicting the development of renal dysfunction, and to a kit for use in making such a prediction.

Apart from the direct adverse impact of physical trauma on the body (e.g. from lesions caused by surgery or car crashes, or from surgical procedures such as blood bypass through a heart-lung machine), subjects suffering physical trauma often develop acute renal dysfunction. Other causes of a similar acute renal dysfunction include prolonged hypotensive states (e.g. associated with mucosal gut ischaemia and endotoxin translocation from gut to circulation), sepsis and septic shock syndromes.

In a population of patients who have normal renal function, diagnosis of post-trauma, hypotensive-induced, sepsis-induced, and/or septic shock syndrome-induced renal dysfunction can be made on the basis of a fall in Glomerular Filtration Rate (GFR) as compared with the normal or baseline GFR; as measured, for example by the MDRD test (explained in more detail below). The limitation of a diagnosis or prognosis based on such measurements is that it usually takes several days for MDRD estimated GFR values to fall. When the GFR fall is detected, it is often too late to institute therapeutic measures to obviate further deterioration in renal function. The challenge facing for example the peri-operative physician or intensive care physician is to identify a biological marker of renal dysfunction 48 hours before such dysfunction materialises (i.e. while there is still a possibility of preventative measures being taken in the intensive care unit; such as running such patients on supra-normal blood pressures, an intervention which in its own right is not without risk in the postoperative context, unless justified by the presence of an even greater risk of impending renal failure such as could be identified by the test according to the present invention).

It is well documented that trauma to the body induces an acute (often transient) plasma pro-inflammatory response. It has been shown that the magnitude of this acute plasma pro-inflammatory response correlates with post-trauma renal dysfunction (Gormley et al., Anesthesiology, 2000, 93). Other causes of a similar acute reno-toxic pro-inflammatory response include prolonged hypotensive states (associated with mucosal gut ischaemia and endotoxin translocation from gut to circulation), or sepsis and septic shock syndromes, all of which are usually either preceded by or associated with a systemic inflammatory response (SIRS) characterised by acute increases in pro-inflammatory mediators in the blood. A mechanism for how such acute pro-inflammatory responses when filtered from the blood damage renal tubules was suggested by Chatterjee who demonstrated in vitro that TNF-[alpha] applied to proximal tubules in cell culture leads to cell damage (Markewitz, J Clin Invest 1993; 91; Chatterjee et al., Exp Nephrol 1999; 7:438-8). Following challenge with the combination of inflammatory cytokines IL-1 beta, TNF-alpha, and IFN-gamma, in vitro proximal tubular cells exhibit a time-dependent increase in inducible NO synthase induction and corresponding NO production to cytotoxic concentration, an effect which was inhibited by L-NMMA (Chatterjee et al., Exp Nephrol 1999; 7:438-8). Stimulation of rat kidney epithelial cells with TNF-alpha and IFN-gamma dramatically increased the level of inducible nitric oxide synthase mRNA (Markewitz, J Clin Invest 1993; 91).

Numerous publications show that levels of urinary anti-inflammatory cytokines show dramatic increases after trauma, and in fact mirror the aforementioned increase in level of pro-inflammatory responses. See, for example: —Gormley et al. Cytokine, January 2002, 21 17(2). Further to this, it has been demonstrated that the magnitude of the post-trauma increases in anti-inflammatory cytokines correlate with the magnitude of renal injury and dysfunction. See, for example: —Litalien et al., Pediatr. Nephrol., November 1999, 13(9); Gretchen et al., Anesthesiology, November 2000, Gormley et al., Anesthesiology, 2000, 93, and; European Patent Publication No. 1 962 092 A (Renovar, Inc.). It is clear from the presentation of these results in the aforementioned publications that a relatively large post-trauma anti-inflammatory cytokine level is proposed as a directly proportional marker for renal dysfunction.

Alternative studies have suggested instead that renal dysfunction can be determined by measuring the change in the level of anti-inflammatory cytokines from before a physical trauma to after a physical trauma. This analysis obviously requires the sampling and evaluation of anti-inflammatory cytokine level both before and after a physically traumatic event.

The inventors have been surprised to find that when they analysed the anti-inflammatory cytokine responses of a large group of post-trauma subjects that a population of those subjects presented with only a relatively low anti-inflammatory cytokine level following physical trauma, as opposed to the expected large anti-inflammatory cytokine level previously reported and as experienced by the majority of subjects. On further analysis of this subgroup, it was surprising to find that its members were at elevated risk of developing renal dysfunction when compared to those that showed the expected large anti-inflammatory cytokine level following physical trauma. Such findings are contrary to the previously accepted conclusion that large post-trauma urinary anti-inflammatory cytokine levels correlate with the magnitude of renal injury and dysfunction.

The inventor's surprising discovery also demonstrates that one can predict renal dysfunction by sampling and analysis of anti-inflammatory cytokines at only a single point, i.e. after the physical trauma. Such analysis is therefore simpler to carry out than studies that indicate that the measurement of both pre- and post-trauma change of anti-inflammatory cytokine levels is required. Measuring only post-trauma anti-inflammatory cytokine levels is particularly advantageous when trying to predict the development of renal dysfunction following unexpected events such as physical trauma induced by a car crash; i.e. when measuring pre-trauma anti-inflammatory cytokine levels is impossible.

The inventors have, following extensive experimentation, provided evidence in support of the concept that by monitoring for a low level of anti-inflammatory cytokine post-trauma or hypotensive subject, or in a subject suffering from sepsis or septic shock syndrome, one can arrive at a prognostic method for renal dysfunction.

Accordingly, in a first aspect of the present invention, there is provided a method for predicting the development of renal dysfunction in a subject following physical trauma, hypotension, sepsis and/or septic shock syndrome, wherein the method comprises the steps of: —
  a. determining the level of an anti-inflammatory cytokine present in a sample taken from the subject after physical trauma, after a hypertensive event, after sepsis, and/or after septic shock syndrome;
  b. predicting the development in the subject of renal dysfunction on the basis of the level of an anti-inflammatory cytokine determined in step a).

The method of the present invention predicts the likelihood of the subject developing post-event (i.e. post-physical trauma, post-hypotensive event, or after the development of sepsis or septic shock syndrome) renal dysfunction. The method is therefore a prognostic method. Subjects may be determined to have a greater than normal chance of developing renal dysfunction when they present with a level of anti-inflammatory cytokines as determined by step a) that is lower than the normal level of anti-inflammatory cytokine. Subjects may be determined to have a lower than normal chance of developing renal dysfunction when they present with a level of anti-inflammatory cytokine as determined by step a) that is higher than the normal level of anti-inflammatory cytokine.

A normal level of anti-inflammatory cytokine is the post-event level presented by a control group of individuals that do not have renal dysfunction on the fifth day following physical trauma, following or during a hypotensive event, following or during sepsis, and/or following or during septic shock syndrome. All of the control individuals will have sustained some degree of sub-clinical renal injury because of the aforementioned events, but will not have had clinically significant renal injury. Determining whether or not an individual has renal dysfunction is a clinical question well within the abilities of the skilled person. However, in the interests of clarity, renal dysfunction is characterised by a reduction in the capacity to excrete metabolic products which accumulate systemically and are detectable clinico-pathologically by renal function tests (in progressed states, renal dysfunction may be acute kidney failure, uremia or chronic renal damage). For example, the MDRD method of determining renal function is described below. The control group may experience the same or similar event (i.e. the same or similar trauma, hypotensive event, sepsis, and/or septic shock syndrome) to the subject being diagnosed. The control group may comprise 30 individuals or more. The control group may comprise 300 individuals or more.

The normal level may be predetermined (ie normal post-event level). Not wishing to be restricted further, but in the interests of clarity, a normal level of IL1ra may be 22700 pgml$^{-1}$ or above. A normal level of TNFsr2 may be 20000 pgml$^{-1}$, or above. A normal level of TNFsr1 may be 20000 pgml$^{-1}$, or above.

Subjects that present with an anti-inflammatory cytokine level determined in step a) that is progressively less than 100% that of the normal level for the anti-inflammatory cytokine are at progressively greater than normal risk of developing renal dysfunction. Thus, when the anti-inflammatory level determined in step a) is 95% or less, 90% or less, 80% or less, 70% or less, 60% or less, 50% or less, 40% or less, 30% or less, 20% or less, or 10% or less that of the normal level the subject is at greater than normal risk of developing renal dysfunction. Such subjects may be at greater than normal risk of having renal dysfunction 5-days following physical trauma, following or during a hypotensive event, following or during sepsis, and/or following or during septic shock syndrome.

If the level of IL1ra determined in step a) is less than 12000 pgml$^{-1}$, it would be predicted that the subject will develop renal dysfunction. If the level of TNFsr2 determined in step a) is less than 11500 pgml$^{-1}$, it would be predicted that the subject will develop renal dysfunction.

Renal dysfunction induced by physical trauma, hypotension, sepsis and/or septic shock syndrome may be further characterised by pro-inflammatory responses that are induced following these events. Such inflammatory responses commonly follow the pattern of a classical systemic inflammatory response (SIRS). Thus, the renal dysfunction to be prognosed according to the present invention may be those that are induced by an acute (possibly transient) urinary pro-inflammatory response (for example, elevated urinary levels of IL-18 and/or of neturophil gelatinase-associated lipocalin (NGAL)).

The renal dysfunction to be prognosed may be early renal dysfunction, late renal dysfunction, or general renal dysfunction. Early renal dysfunction occurs within two days of the event that induces the renal dysfunction. Late renal dysfunction occurs 5 days or later after such an event Renal dysfunction may be defined as a 25% or more decrease from normal glomerular filtration rate. Normal glomerular filtration rate is the pre-even rate. Glomerular filtration rate may be established in accordance with the MDRD study group formula. Such acute forms of renal dysfunction can be distinguished from autoimmune mediated chronic renal dysfunction, a condition that is clinically apparent over a prolonged period of time in parallel with the coexisting autoimmune condition (i.e. there is no requirement for a biological marker to predict the development of renal dysfunction occurring a few days later because the renal dysfunction is already well established).

The sample taken from the subject may be any sample capable of being analysed for the level of anti-inflammatory cytokine therein. For example, the sample may be a urine sample, a blood sample or a plasma sample. A urine sample is particularly preferred.

The sample analysed in step a) may be obtained from the subject within 24 hours of the event (i.e. physical trauma, hypotensive event, onset of sepsis and/or onset of septic shock syndrome). The sample will optimally be obtained within 12 to 24 hours of the event Step a) may be preceded by a step of obtaining a sample from the subject.

The predicting of the development in the subject of renal dysfunction in the present invention is based on the determination of the level of an anti-inflammatory cytokine present in a sample after the recited events. Consequently, it would be clear that the level of an anti-inflammatory cytokine present in a sample after the recited events may be the only cytokine level required to be determined in order to make the prediction according to the present invention. It is also therefore clear that the methods of the present invention do not require the level of an anti-inflammatory cytokine present in a sample prior to the recited events to be determined in order to make the prediction according to the present invention.

A physical trauma is the impact on the body from external forces applied to the body, for example: —lesions caused by surgery or by blows or cuts to the body (such as might be experienced during a car crash), or; the impact on the blood as it interacts with the foreign surface of a heart-lung bypass machine. Renal dysfunction induced by physical trauma may be postoperative renal dysfunction. The post-operative renal dysfunction may be following cardiac, cardiovascular or cardiopulmonary surgery.

Whether or not an individual has hypotension is a clinical question and therefore well within the skill of an ordinary person in the art. For the avoidance of doubt however hypotension in adults may be defined as a systolic blood pressure <80 mmHg, or a mean arterial pressure (MAP)<50 mmHg. The hypotension may be prolonged, for example for over 2 hours.

Whether or not an individual has sepsis is a clinical question and therefore well within the skill of an ordinary person in the art. For the avoidance of doubt however, sepsis may be considered present if infection is highly suspected or proven and two or more of the following systemic inflammatory response syndrome (SIRS) criteria are met:

1. Heart rate >90 beats per minute (tachycardia);
2. Body temperature <36° C. (97° F.) or >38° C. (100° F.) (hypothermia or fever);
3. Respiratory rate >20 breaths per minute or, on blood gas, a $P_aCO_2$ less than 32 mm Hg (4.3 kPa) (tachypnea or hypocapnia due to hyperventilation); and
4. White blood cell count <4,000 cells/mm$^3$ or >12,000 cells/mm$^3$ (<4×10$^9$ or >12×10$^9$ cells/L), or greater than 10% band forms.

Whether or not an individual has septic shock is a clinical question and therefore well within the abilities of an ordinary person skilled in the art. For the avoidance of doubt however, septic shock may be defined by the presence of the following two criteria:

1. Evidence of infection, through a positive blood culture; and
2. Refractory hypotension—hypotension despite adequate fluid resuscitation and cardiac output. In adults it is defined as a systolic blood pressure <90 mmHg, or a MAP <60 mmHg, before institution of required resuscitative inotropic support, or a reduction of 40 mmHg in the systolic blood pressure from baseline. In children it is BP<2 SD of the normal blood pressure.

Whether or not an individual has SIRS is a clinical question and therefore well within the abilities of an ordinary person skilled in the art. For the avoidance of doubt however SIRS may be diagnosed when two or more of the following are present:

1. Heart rate >90 beats per minute
2. Body temperature <36 or >38° C.
3. Tachypnea (high respiratory rate) >20 breaths per minute or, on blood gas, a $P_aCO_2$<4.3 kPa (32 mm Hg)
4. White blood cell count <4000 cells/mm$^3$ or >12000 cells/mm$^3$ (<4×10$^9$ or >12×10$^9$ cells/L), or the presence of greater than 10% immature neutrophils.

The anti-inflammatory cytokine may be any cytokine capable of suppressing inflammatory responses in the body and that can be detected in a sample (e.g. the urine). The anti-inflammatory cytokine may be one locally released in renal tissue. The anti-inflammatory cytokine may be TNFsr1, TNFsr2 or IL-1 ra.

The method may involve analysis of the levels of more than one type of anti-inflammatory cytokine. For example, the methods according to the present invention may further comprise the steps of: — a') determining the level of one or more additional anti-inflammatory cytokine present in a sample taken from the subject after physical trauma, after a hypotensive event, after sepsis, and/or after septic shock syndrome;

b') predicting the development in the subject of developing renal dysfunction on the basis of the level of an anti-inflammatory cytokine determined in step a) and a").

The risk of the subject developing renal dysfunction is greater when both (i) the level of anti-inflammatory cytokine is determined by step (a) is lower than the normal level, and (ii) the level of anti-inflammatory cytokine as determined by step (a') is lower than the normal level.

Any combination of the aforementioned anti-inflammatory cytokines may be used in such a method. For example the anti-inflammatory cytokine determined in step a) may be IL-1 ra and the one or more anti-inflammatory cytokine determined in step a') may be TNFsr2.

Pro-inflammatory markers of impending renal dysfunction have been identified; pro-inflammatory mediators NGAL and IL-18 (Mishra et al., Lancet, 2005; 365:1231-38). Elevations of these substances in the urine of children have been associated with heightened risk of developing renal dysfunction several days later. Based on the hypothesis presented by the present inventors, however, establishing that an individual has an elevated pro-inflammatory response alone may not be sufficient to establish the risk of developing renal dysfunction.

The method may involve the post-event analysis of the levels of one (or more than one type of) anti-inflammatory cytokine and one or more pro-inflammatory mediator.

The pro-inflammatory mediators may be any mediator capable of inducing an inflammatory response in the body, that is implicated in the development of renal dysfunction and that can be detected in the urine. The pro-inflammatory mediators may be IL-18 and/or NGAL.

In a further aspect of the present invention, there is provided a kit for use in the methods of the preceding claims, wherein the kit comprises: —

(a) one or more reagents for the detection of the amount of one or more anti-inflammatory cytokine;

(b) instructions for using the one or more reagents for detecting the one or more anti-inflammatory cytokines.

The kit may further comprise one or more reagents for the detection of one or more pro-inflammatory mediator, and instructions for using the one or more reagents for detecting the one or more pro-inflammatory mediator.

The kit may further comprise instructions for using the detecting of the one or more anti-inflammatory cytokines in order to arrive at a prognosis for renal dysfunction. The instructions may be in accordance with the steps for prognosis of renal dysfunction provided in the first aspect of the present invention. The kit may further comprise instructions for using the detecting of the one or more pro-inflammatory mediator in order to arrive at a prognosis for renal dysfunction. As the instructions and reagents are to be capable of being used in order to practice the methods described above in accordance with the first aspect of the present invention, all features of the first aspect of the present invention may be included in the second aspect of the present invention, where the context permits. Consequently, for example, the anti-inflammatory cytokines (or combinations thereof) and the pro-inflammatory mediators mentioned in the first aspect of the present invention may be those recited above in the second aspect of the present invention.

In a third aspect of the present invention there is provided a method of treating renal dysfunction induced by physical trauma, hypotension, sepsis and/or septic shock syndrome, wherein the method includes the steps of: (i) prognosing renal dysfunction according to any of the methods of the first aspect of the present invention; and (ii) when the subject is identified to be at increased risk of developing renal dysfunction, applying therapeutic measures to treat or obviate the impending renal dysfunction. The advantage of such a method over current therapeutic interventions is that therapy may be administered at a stage when full renal failure may be prevented. The therapeutic measures applied in step (ii) may be: maintaining a supra-normal blood pressure; ensuring adequate tissue oxygen delivery; administration of steroids; renal replacement therapy; dialysis; or any combination thereof. A further advantage of this invention would be to allow intensive care managers to identify early in the intensive care stay of the patient those individuals who are likely to spend longer in intensive care than would otherwise be anticipated providing earlier planning for staff deployment.

A number of lists are provided above in which optional features for each of the aspects of the present invention are provided. Each member of the list is contemplated individually as a potential feature of the present invention.

The present invention will now be described, by way of example, with reference to the accompanying figures, in which: —

EXPERIMENTAL METHODS

Figure 1:
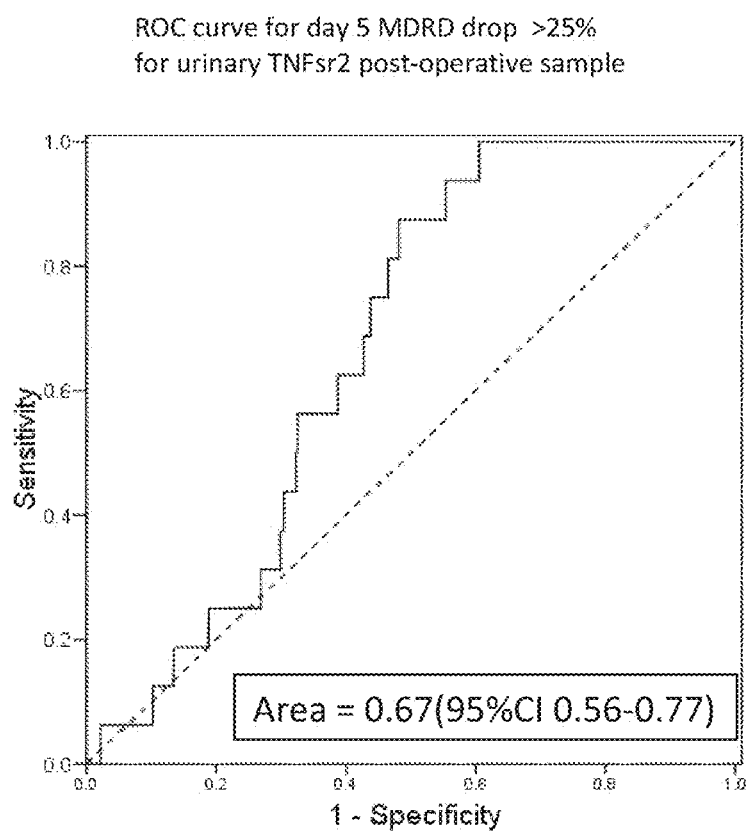
FIG. 1 shows receiver/operator characteristics (ROC) curve for post-operative urinary TNFsr2 showing sensitivity and specificity to distinguish patients with and without renal dysfunction as defined by MDRD eGFR drop at day 5 post-surgery of more than 25% from the pre-surgery value.

Four hundred and eight consecutive patients undergoing elective cardiac surgery were studied. The patients were recruited within the Cardiac Surgical Unit of the Royal Victoria Hospital Belfast in Northern Ireland (n=304) and Papworth Hospital NHS Foundation Trust in Cambridge, England (n=104). Local ethical committee approvals were received and written informed patient consent was obtained. Exclusion criteria included pre-operative dialysis dependent renal failure, significant renal disease (eGFR <40 ml min$^{-1}$) or diabetes mellitus. Patients on pre-operative angiotensin conversion enzyme (ACE) inhibitor therapy were not excluded from this study. The anaesthetic technique in both centers was based on the use of propofol and fentanyl. Isoflurane was used in most patients either as an adjunct anaesthetic agent or to control blood pressure. Pancuronium was used to provide muscle relaxation. Post-operative analgesia was with morphine infusion.

In the 408 elective cardiac surgery patients 24 hour post-operative urinary IL1ra and TNFsr2 was measured. The post-operative urinary response was compared for each cytokine in patients grouped according to presence or absence of renal dysfunction defined as a drop from baseline estimated glomerular filtration rate (eGFR) of greater than 25% (as calculated by the method of modification of diet in renal disease (MDRD)) occurring within (1) the first 24 and (2) 48 postoperative hours (early renal dysfunction), (3) on the fifth postoperative day (late renal dysfunction) or (4) at any time throughout the 5 day post-operative period (early and late combined)).

Cytokines Analysis (ELISA)

Cytokines are measured by R&D systems Quantikine solid phase ELISA technique. This system consists of a conjugate, standard, assay diluent, calibrator diluent, wash buffer concentrate, colour reagent A, colour reagent B, and a stop solution. Reagents should be at the room temperature before beginning the assay. The microplate-consists of 96 wells. This microplate is coated with capture antibody. To each well assay diluent is added. Standards in duplicate and the samples are added to the plate and incubated for 2 h at room temperature. Any analyte present in the sample is bound by the capture antibody (immobilized antibody). After the incubation, the plate is aspirated and washed four times with the supplied wash buffer to washout any unbound materials. After washing, horseradish protease (HRP) labelled detection antibody (conjugate) is added to the plate and further incubated at room temperature. Once again, after the incubation the plate is aspirated and washed 4 times. Any unbound detection antibody is washed away. In the next step prepared substrate solution tetramethylbenzidine (TMB) is added to the wells and a blue colour develops in proportion to the amount of analyte present in the sample. After 20 minutes incubation the colour develops (blue) proportional to the cytokine concentration. For analysis colour development is stopped turning the colour in the wells to yellow. The absorbance of the colour at 450 nm is measured which is read in the microplate reader.

Urinary samples for measurement of urinary IL-1ra and TNFsr2 were obtained at 24 hours after cessation of cardiopulmonary bypass or revascularisation.

Measurement of Renal Dysfunction

In 1989 Kopple et al as part of the Modification of Diet in Renal Disease study group published their findings investigating the impact of nutritional status on chronic renal insufficiency in 95 patients. The effects on progression of renal disease of a control diet of only mild dietary protein restriction were compared with 3 study diets of varying degrees of protein restriction and reduced phosphorus intake. The authors found that malnutrition and lower energy intake characterised patients with the lower GFR levels. There were some gender differences with men demonstrating a correlation between GFR and arm muscle area and percentage standard body weight especially at the onset of the experimental diets. In women, GFR correlated with dietary energy intake [Kopple et al., Kidney Int Suppl 1989; 27]. A logical development of this study from the MDRD group was the idea that analysis of patients' age weight, gender and ethnicity together with serum creatinine would allow GFR to be estimated. This assumption recognised that serum creatinine concentration alone does not adequately reflect renal function but should be considered along with the factors identified as influencing renal function in Kopple's study.

To develop the prediction equation 1628 patients were enrolled in the baseline period, of which 1070 were randomly selected as the training sample whereas the remaining 558 patients constituted the validation sample. The authors then used stepwise regression to the training sample to develop the equation which was then tested and compared with the Cockcroft and Gault formula and creatinine clearance measurements in the validation sample.

It was found that several measured variables were associated with a lower GFR. These included higher serum creatinine, higher serum urea and lower serum albumin levels concentrations. Independent variables associated with lower GFR included older age group, female gender and non-black ethnicity ($P<0.001$ for all factors).

The multiple regression models explained 90.3% of the variance in the logarithm of GFR in the validation sample. Measured creatinine clearance overestimated GFR by 19%, and creatinine clearance predicted by the Cockcroft-Gault formula overestimated GFR by 16%. After adjustment for this overestimation, the percentage of variance of the logarithm of GFR predicted by measured creatinine clearance or the Cockcroft-Gault formula was 86.6% and 84.2%, respectively.

MDRD study group estimated GFR is calculated from the following formula: $X = 32788 \times \text{creatinine} - 1.154 \times \text{age} - 0.203 \times \text{constant}$ where the constant is 1 for white males, 0.724 for females, and 1.21 for African Americans.

MDRD estimated GFR in the present study was calculated from the above formula. According to the above formula MDRD GFR was calculated at preop day 0 and at post operative days 1, 2 and 5. For each separate post op day as well as all post op days together patients can be divided into normal and abnormal renal function groups where "normal" and "abnormal" were defined by those who sustained falls in MDRD GFR of less than or greater than 25% of baseline respectively.

In summary then for post surgery cytokine values were compared between the normal and abnormal groups where normality and abnormality were defined according to the 4 definitions mentioned below.

Definition 1: 'Abnormality' is defined as having day 1 MDRD >25% drop from baseline. (Early renal dysfunction).

Definition 2. 'Abnormality' is defined as having day 2 MDRD >25% drop from baseline. (Early renal dysfunction).

Definition 3. 'Abnormality' is defined as having day 5 MDRD >25% drop from baseline. (Late renal dysfunction).

Definition 4. 'Abnormality' is defined as having at least one MDRD value >25% drop from baseline during days 1, 2, and 5. (General renal dysfunction).

Statistical Methods

Quantitative variables were summarized as mean and standard deviation except for those with heavily skewed distributions for which median and interquartile range were used. Comparisons between groups were obtained using the independent samples z-test or Mann-Whitney U test for quantitative variables, and the chi-squared test or Fisher's exact test for categorical variables. The ability of cytokine measurements to distinguish patients with and without renal dysfunction in the postoperative period was examined using the receiver-operator characteristic (ROC) curve. The area under this curve provides a measure of discriminatory ability; a value of 1 indicates perfect discrimination while a value of 0.5 indicates no more discriminatory ability than would be expected by chance.

Results

1. Numbers of Patients in Renal Dysfunction and their Characteristics

Figure 3:
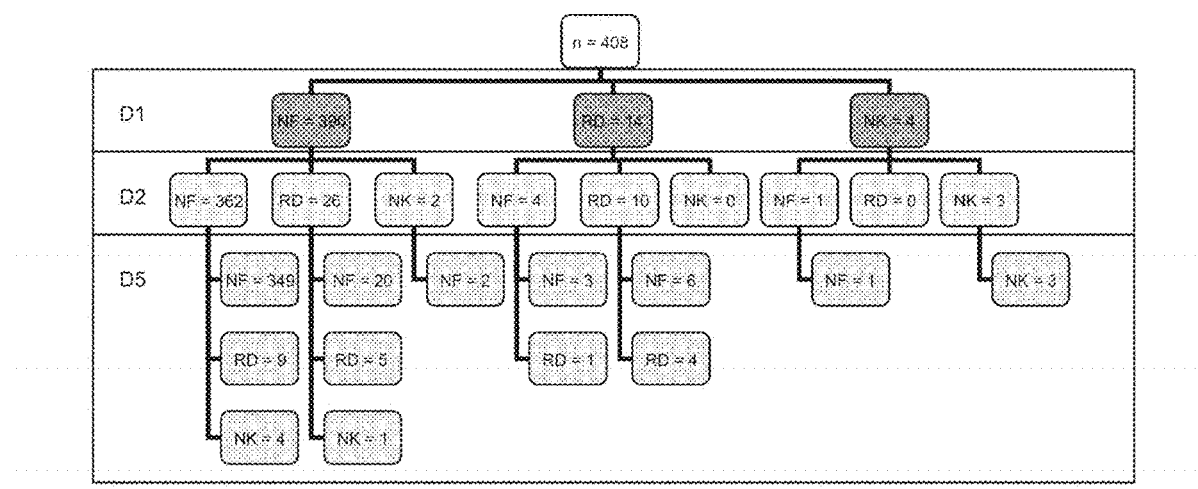
FIG. 3 shows a table demonstrating the number of patients on each day of the study discussed below who had normal renal function (NF), or renal dysfunction (RD) as defined by greater than 25% MDRD drop from base line on that day, or for whom renal function data was not know (NK).

The numbers of patients who developed renal dysfunction on postoperative days 1, 2 and 5 are illustrated in FIG. 3. Table 1 shows the characteristics of patients categorized according to presence or absence of renal dysfunction defined by >25% drop from baseline eGFR at any time during the 5 day postoperative period. Renal dysfunction was more likely in patients who had increased weight, male gender or who had not been given an intra-operative dopamine infusion (Table 1). A requirement for postoperative resternotomy for bleeding/cardiac tapenade or post-operative adrenaline infusion was linked with renal dysfunction. Development of renal dysfunction significantly prolonged length of stay in the intensive care/high dependency unit (Table 1).

TABLE 1

The table shows pre- and peri-operative characteristics of patients with and without renal dysfunction as defined by >25% drop from baseline eGFR at any time during the postoperative period (mean +/− SD or n (%)).

| | Patients with MDRD eGFR drop ≤25% at all times (N = 349) | Patients with MDRD eGFR drop >25% at any time (N = 49) | P value |
|---|---|---|---|
| Baseline MDRD eGFR (ml/min/1.73 m$^2$) | 73.8 +/− 15.3 | 75.9 +/− 24.5 | 0.57 |
| Age (years) | 62.6 +/− 10.5 | 65.6 +/− 10.3 | 0.06 |
| Weight (kg) | 77.1 +/− 13.6 | 82.8 +/− 15.7 | 0.02* |
| Height (m) | 1.69 +/− 0.10 | 1.71 +/− 0.08 | 0.06 |
| BMI (kg/m$^2$) | 27.0 +/− 4.0 | 28.2 +/− 4.5 | 0.08 |
| Male Gender | 237/349 (68%) | 42/49 (86%) | 0.01* |
| Operation time (min) | 252 +/− 51 | 259 +/− 91 | 0.59 |
| CPB time # (min) | 95 +/− 34 | 99 +/− 41 | 0.52 |
| Cross clamp time †(min) | 62 +/− 28 | 62 +/− 25 | 0.81 |
| Beta blocker | 226/349 (65%) | 33/49 (67%) | 0.72 |
| Calcium Antagonist | 83/348 (24%) | 14/49 (29%) | 0.47 |
| Nitrate | 162/349 (46%) | 20/49 (41%) | 0.46 |
| K channel blocker | 119/349 (34%) | 13/49 (27%) | 0.29 |
| ACEI | 152/349 (72%) | 24/49 (49%) | 0.47 |
| ATII receptor blocker | 13/349 (4%) | 4/49 (8%) | 0.14 |
| Intra-operative phenylephrine | 223/349 (64%) | 30/49 (61%) | 0.72 |
| Any intra-operative intotrope | 159/348 (46%) | 18/49 (37%) | 0.24 |
| Intra-operative dopamine | 118/348 (34%) | 7/49 (14%) | 0.006* |
| Intra-operative noradrenaline | 36/347 (10%) | 6/49 (12%) | 0.69 |
| Intra-operative adrenaline | 17/349 (5%) | 3/49 (6%) | 0.72 |
| Intra-operative milrinone | 25/349 (7%) | 3/49 (6%) | 1.00 |
| Intra-operative IABP | 3/348 (1%) | 0/49 (0%) | 1.00 |
| Any post-operative inotrope | 156/349 (45%) | 20/49 (41%) | 0.61 |
| Post-operative dopamine | 145/348 (42%) | 16/49 (33%) | 0.23 |
| Post-operative noradrenaline | 26/349 (7%) | 7/49 (14%) | 0.16 |
| Post-operative adrenaline | 17/349 (5%) | 6/49 (12%) | 0.05* |
| Post-operative milrinone | 28/349 (8%) | 2/49 (4%) | 0.56 |

TABLE 1-continued

The table shows pre- and peri-operative characteristics of patients with and without renal dysfunction as defined by >25% drop from baseline eGFR at any time during the postoperative period (mean +/− SD or n (%)).

|  | Patients with MDRD eGFR drop ≤25% at all times (N = 349) | Patients with MDRD eGFR drop >25% at any time (N = 49) | P value |
|---|---|---|---|
| Intra-operative IABP | 1/349 (0%) | 0/49 (0%) | 1.00 |
| Intra-operative PRBC | 76/348 (25%)) | 13/49 (27%) | 0.46 |
| Intra-operative FFP | 5/349 (1%) | 2/49 (4%) | 0.21 |
| Intra-operative platelets | 11/349 (3%) | 3/49 (6%) | 0.40 |
| Post-operative PRBCs | 150/348 (43%) | 26/49 (53%) | 0.19 |
| Post-operative FFP | 41/349 (12%) | 5/49 (10%) | 0.75 |
| Post-operative platelets | 47/349 (13%) | 5/49 (10%) | 0.53 |
| Intra-operative hypotension >5 minutes | 2/349 (1%) | 0/49 (0%) | 1.00 |
| Post-operative hypotension >5 minutes | 2/349 (1%) | 2/49 (4%) | 0.08 |
| Re-sternotomy for bleeding | 12/349 (3%) | 5/49 (10%) | 0.05* |
| Intubation time ‡ (hr) | 20 (14-24) | 19 (11-24) | 0.16 |
| CSICU discharge in 48 hrs | 315/347 (91%) | 37/49 (76%) | 0.001** |

Abbrevations used in this table: standard deviation (SD); fresh frozen plasma (FFP) packed red blood cells (PRBCs); intra-aortic balloon pump (IABP); cardiac surgical intensive care unit (CSICU); cardiopulmonary bypass (CPB); angiotensin converting enzyme inhibitor (ACEI); angiotensin-2 (AG-II).
*P < 0.05
**P < 0.01;
in 362 patients on CPB;
†in 359 patients on cross clamp
‡ Median (interquartile range)

2. Cytokine Results

Figure 2:
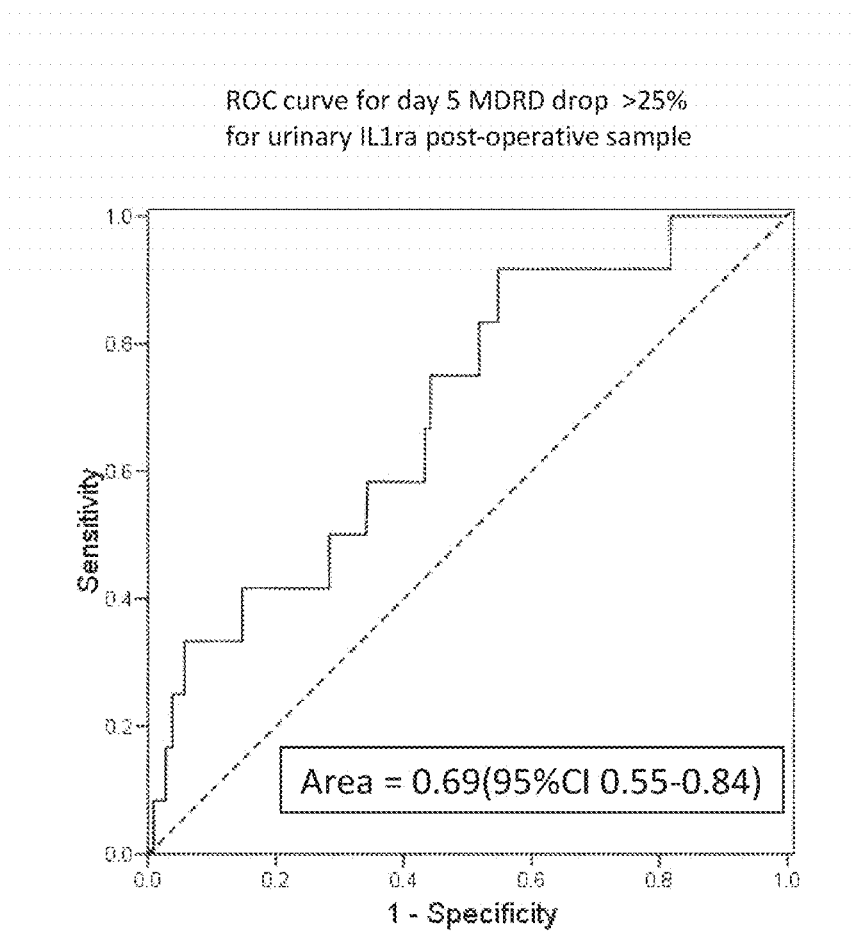
FIG. 2 shows receiver/operator characteristics (ROC) curve for post-operative urinary IL1ra showing sensitivity and specificity to distinguish patients with and without renal dysfunction as defined by MDRD eGFR drop at day 5 post-surgery of more than 25% from the pre-surgery value.

Cytokine results are illustrated in Table 2. There were significantly lower post-operative 24 hour urinary IL1ra and TNFsr2 levels in those patients who developed late (day 5) renal dysfunction (Table 2). The relative value of lower than normal post-operative urinary IL1ra and TNFsr2 in predicting day 5 (late) renal dysfunction is demonstrated in the relevant receiver operator characteristic (ROC) curves shown in FIGS. 1 and 2.

3. Discussion.

The main findings of this study are:

If patients are grouped into those with and without renal dysfunction in the fifth post-operative day, the abnormal renal function group had significantly lower 24 hour urinary IL1ra and TNFsr2 than the normal renal function group.

TABLE 2

Table showing 24 hours post-operative urinary cytokine concentrations (median and interquartile range)IQR) in patients categorised according to MDRD estimated 25% eGFR percentage drop from pre-operative baseline at any time post-operatively (Any MDRD >25% drop) as well as on post-operative day 1 (MDRD D1 >25% drop), day 2 (MDRD D2 >25% drop) and day 5 (MDRD D5 >25% drop) (*P < 0.05).

| | Any MDRD >25% drop | | | | |
|---|---|---|---|---|---|
| | No | | Yes | | |
| Cytokine (pg ml$^{-1}$) | n | Median (IQR) | n | Median (IQR) | P value |
| IL1ra (post-operative) | 337 | 22891 (9526-48518) | 40 | 18327 (7081-31354) | 0.17 |
| TNFsr2 (post-operative) | 342 | 20039 (9132-30693) | 44 | 13955 (9990-21838) | 0.044 |

| | MDRD D1 >25% drop | | | | |
|---|---|---|---|---|---|
| | No | | Yes | | |
| Cytokine (pg ml$^{-1}$) | n | Median (IQR) | n | Median (IQR) | P value |
| IL1ra (post-operative) | 370 | 22017 (9593-48060) | 13 | 14553 (6109-23168) | 0.15 |
| TNFsr2 (post-operative) | 379 | 19345 (9280-30519) | 13 | 12967 (7926-22229) | 0.22 |

| | MDRD D5 >25% drop | | | | |
|---|---|---|---|---|---|
| | No | | Yes | | |
| Cytokine (pg ml$^{-1}$) | n | Median (IQR) | n | Median (IQR) | P value |
| IL1ra (post-operative) | 367 | 22687 (9594-48006) | 12 | 12332 (1777-22316) | 0.02* |
| TNFsr2 (post-operative) | 372 | 19688 (9204-30629) | 16 | 11529 (8054-17261) | 0.02* |

TABLE 2-continued

Table showing 24 hours post-operative urinary cytokine concentrations (median and interquartile range)IQR) in patients categorised according to MDRD estimated 25% eGFR percentage drop from pre-operative baseline at any time post-operatively (Any MDRD >25% drop) as well as on post-operative day 1 (MDRD D1 >25% drop), day 2 (MDRD D2 >25% drop) and day 5 (MDRD D5 >25% drop) (*P < 0.05).

| | MDRD D2 > 25% drop | | | | |
|---|---|---|---|---|---|
| | No | | Yes | | |
| Cytokine (pg ml$^{-1}$) | n | Median (IQR) | n | Median (IQR) | P value |
| IL1ra (post-operative) | 349 | 21348 (9445-47883) | 33 | 20306 (10883-46321) | 0.79 |
| TNFsr2 (post-operative) | 358 | 19449 (9178-30595) | 33 | 13840 (9931-24404) | 0.16 |

The invention claimed is:

1. A method of treating a subject at increased risk of renal dysfunction induced by at least one of physical trauma, hypotension, sepsis, and septic shock syndrome, wherein the method includes the step of:
   a) obtaining a urine sample from a subject after the at least one of physical trauma, hypotension, sepsis and septic shock syndrome;
   b) detecting the anti-inflammatory cytokine present in the urine sample obtained in step a), wherein the anti-inflammatory cytokine is selected from the group consisting of IL-1ra, TNFsr1 and TNFsr2 and any combination thereof;
   c) detecting the anti-inflammatory cytokine in a post-event normal control;
   d) calculating the level of anti-inflammatory cytokine detected in step b) relative to the level of anti-inflammatory cytokine detected in step c);
   e) determining that the subject has a greater than normal chance of developing renal dysfunction induced by physical trauma, hypotension, sepsis and/or septic shock syndrome when the level of anti-inflammatory cytokine determined in step b) is lower than the level of anti-inflammatory cytokine detected in step c); and
   f) applying therapeutic measures to treat or obviate the predicted impending renal dysfunction to the subject wherein the therapeutic measures are selected from maintaining a supra-normal blood pressure; ensuring adequate tissue oxygen delivery; administration of steroids; renal replacement therapy; dialysis; or any combination thereof.

* * * * *